United States Patent

Brunnett et al.

[11] Patent Number: 5,166,961
[45] Date of Patent: Nov. 24, 1992

[54] CT SCANNER HAVING MULTIPLE DETECTOR WIDTHS

[75] Inventors: Carl J. Brunnett, Willoughby Hills; Chris J. Vrettos, Willoughby, both of Ohio

[73] Assignee: Picker International, Inc., Highland Heights, Ohio

[21] Appl. No.: 577,685

[22] Filed: Sep. 4, 1990

Related U.S. Application Data

[63] Continuation-in-part of Ser. No. 260,403, Oct. 20, 1988, Pat. No. 4,965,726.

[51] Int. Cl.⁵ ............................................. H05G 1/60
[52] U.S. Cl. ...................................... 378/19; 378/22; 378/116
[58] Field of Search .................... 378/19, 16, 22, 24, 378/11, 4, 116

[56] References Cited

U.S. PATENT DOCUMENTS

| | | | |
|---|---|---|---|
| 4,292,538 | 9/1981 | Carlson | 378/19 |
| 4,398,092 | 8/1983 | Carlson | 378/19 |
| 4,466,112 | 8/1984 | Covic et al. | 346/244 |
| 4,547,893 | 10/1985 | Gordon | 378/4 |
| 4,947,412 | 8/1990 | Mattson | 378/19 |
| 4,965,726 | 10/1990 | Heuscher et al. | 364/413.13 |

FOREIGN PATENT DOCUMENTS 0139375  5/1985  European Pat. Off. .............. 378/19

Primary Examiner—Janice A. Howell
Assistant Examiner—Don Wong
Attorney, Agent, or Firm—Fay, Sharpe, Beall, Fagan, Minnich & McKee

[57] ABSTRACT

A CT scanner (10) includes a radiation source (12) mounted for rotation about a scan circle (14). A ring of radiation detectors (30) includes narrow detectors ($30_n$) and wide detectors ($30_w$). The narrow and wide detectors are separately sampled ($42_n$, $42_w$) and operated on with different digital filters ($50_n$, $50_w$). The wider detectors have a more limited frequency response (32) which typically includes an out of phase response portion (36); whereas, the output signal from the narrow detector has a higher frequency response (34), i.e. better resolution. The filters ($50_n$, $50_w$) are selected to yield optimum signal to noise ratio. When the data is merged (60), the resultant data has a modulation transfer function with response (62) which has a higher frequency component or improved resolution relative to response (70) that would be obtained from detectors of uniform width of the average of the narrow and detector widths.

14 Claims, 3 Drawing Sheets

CT SCANNER HAVING MULTIPLE DETECTOR WIDTHS

This application is a continuation-in-part of U.S. application Ser. No. 260,403, filed Oct. 20, 1988, entitled, "CT Scanner with Segmented Detector Array", now U.S. Pat. No. 4,965,726.

BACKGROUND OF THE INVENTION

The present application relates to the art of medical diagnostic imaging in which penetrating radiation is received by an array of radiation sensitive detectors. The invention finds particular application in conjunction with fourth generation computerized tomographic (CT) scanners and will be described with particular reference thereto. However, it is to be appreciated that the invention may also find application in conjunction with other diagnostic imaging modalities.

Heretofore, CT scanners have included a plurality of discrete radiation detectors arranged in a ring or a rotatable ring segment around a patient examination region. Each detector included a radiation sensitive face, such as a scintillation crystal which converted received radiation into a corresponding quantity of light. A solid state photodiode or vacuum tube photomultiplier converted the light emitted by the scintillation crystal into electrical signals indicative of the intensity of emitted light, hence the intensity of received radiation.

The size of the radiation sensitive face was typically one of the most significant parameters determining spatial resolution of the CT scanner. That is, the width of the path or ray of radiation as defined by the x-ray source and the detector was highly dependent upon the width of the detector. Detail within the object or patient being scanned which had physical dimensions approximately equal to or less than the x-ray path width was difficult, if not impossible, to distinguish. By making the width of the radiation detector narrower, the width of the radiation path or ray was narrowed. Narrowing the radiation path decreased the width of the region of the patient which contributed to the resultant electrical signal, hence, improved spatial resolution. Of course, decreasing the width of the radiation sensitive surface also decreased the number of photons of radiation received per unit time, hence, detection efficiency.

In this manner, there is a trade off between radiation dose and resolution when deciding whether to make the detectors wide or narrow. Depending on the nature of the study or diagnostic image desired, either wide or narrow detectors may be advantageous. In order to select between the advantages of wide and narrow detectors, prior scanners have selectively placed an aperture plate or septa in front of the detectors to restrict the radiation impinging thereon. The radiation plates could be removed when the benefits of a wide detector were desired and inserted when the higher resolution benefits of a narrow detector were desired. Moreover, aperture plates of the varying sizes could be configured for mechanical insertion in front of the radiation receiving face of the detectors, enabling any one of a plurality of detector widths to be utilized.

One disadvantage of the use of aperture plates is that the plates or septa that define the aperture block radiation which has traversed the patient from impacting the radiation sensitive face of the detector. Thus, this radiation to which the patient has been exposed does not contribute to the resultant image, reducing dose utilization and radiation detection efficiency. Another approach was to collimate the radiation beam adjacent the radiation source to define a plurality of narrow beams which impinge upon the patient and detectors. This type of collimation was impractical with CT scanners that utilize a large number of closely spaced detectors and/or where relative motion existed between x-ray source and detectors.

Another approach which attempted to combine the dose utilization advantages of a wide detector with the resolution of a narrow detector is illustrated in U.S. Pat. No. 4,398,092 to R. Carlson, et al. This patent discloses a relatively wide detector which is more sensitive to radiation impacting the center of the detector than to radiation impacting the edges. However, this non-uniform weighting of x-ray photons, which results from the non-uniform response of the detector, increases the quantum noise, i.e. the amplitude of the photon statistics, since minimal quantum noise is achieved when all photons are weighted equally. Moreover, in Carlson only those photons near the center of the detector contain useful higher spatial frequency information and hence, the response to higher frequencies is greatly reduced compared to the low frequency response. In fact, at certain spatial frequencies, the non-uniform detector response can actually cause a further decrease in the high frequency response, a condition that can result from a phase reversal in the signal of the edge detected photons. Due to the low response to high frequencies, this system is of limited benefit in scanning patients.

Another technique for reducing the width of the necessary detectors was to place the detector ring of a fourth generation scanner inside of the rotational path of the x-ray tube. This configuration reduced the diameter or circumference of the detector ring, hence the width of the individual detectors. However, this geometry was disadvantageous in that it required a rather complex motion, called nutating, of the detector ring to allow the x-ray beam to pass. This geometry was also susceptible to scatter radiation due to the close proximity of the detectors to the patient.

Moreover, it should be noted that each of these prior art systems use a ring of radiation detectors in which all radiation detectors had the same width in the peripheral direction.

SUMMARY OF THE INVENTION

In accordance with the present invention, a CT scanner is provided in which the detectors have different widths in a peripheral direction around the detector ring.

One advantage of the present invention is that the outputs of each of the different detector widths can be filtered with different filter functions to optimize performance.

A second advantage of the present invention is that the regions of response of detectors where phase reversal occurs can be practically utilized to improve dose efficiency and resolution.

A third advantage of the present invention is that the dose efficiency and the resolution is better than that of a scanner having the same number of uniform width detectors.

Still further advantages will become apparent upon reading and understanding the following detailed description.

BRIEF DESCRIPTION OF THE DRAWINGS

The invention may take form in various components and arrangements of components and in various steps or arrangements of steps. In order to help in understanding the invention, reference will be made to a preferred embodiment wherein the scanner is a fourth generation scanner, and the detectors are of two different alternating widths. The description and figures are only for purposes of illustrating a preferred embodiment and are not to be construed as limiting the invention.

DETAILED DESCRIPTION OF THE PREFERRED EMBODIMENTS

Figure 1:
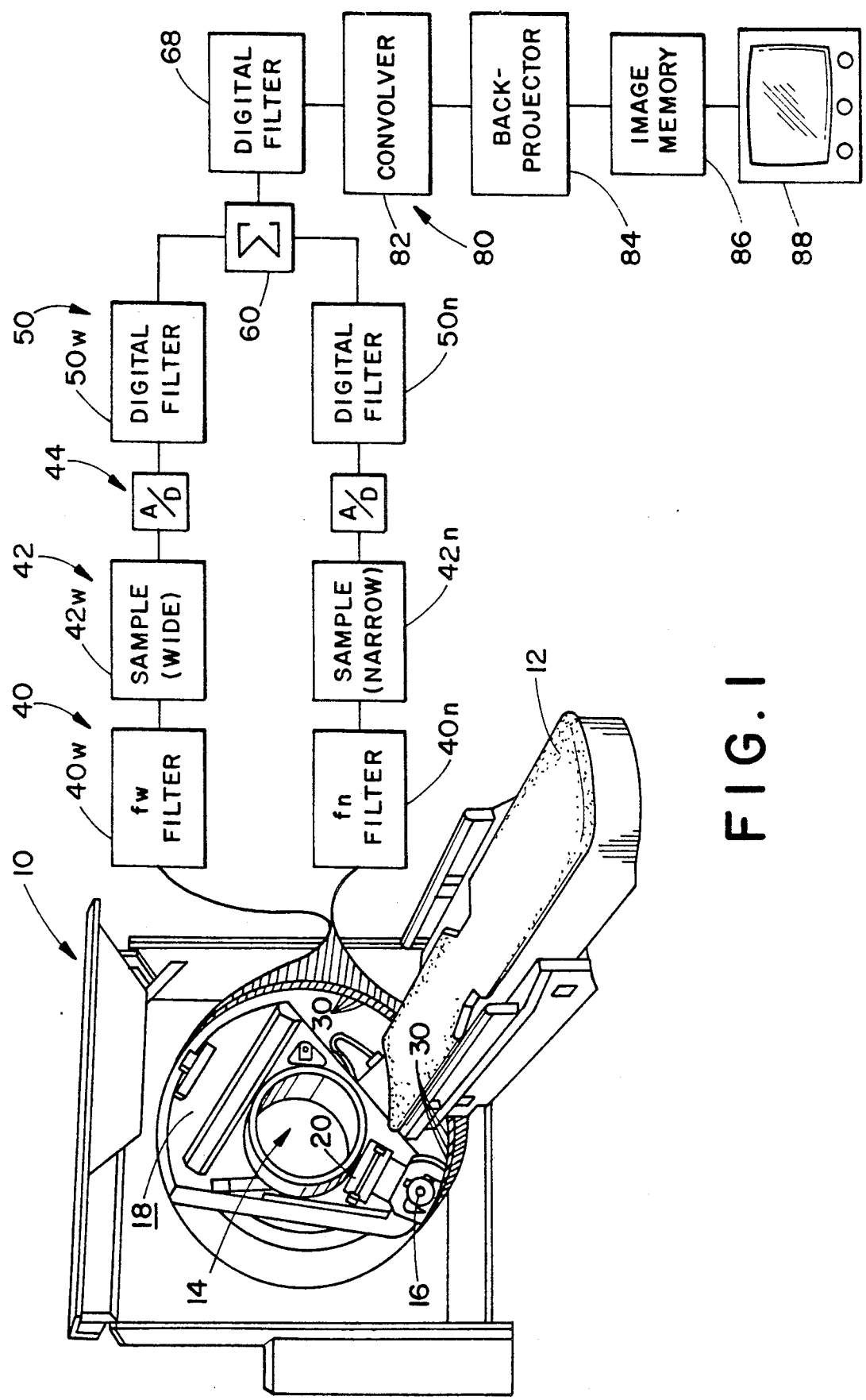
FIG. 1 is a diagrammatic illustration of a CT scanner in accordance with the present invention.

With reference to FIG. 1, a CT scanner 10 selectively images cross sectional slices of a region of a patient supported on a stationary patient couch 12 within a scan circle or examination region 14. In some applications, the patient couch is incremented longitudinally in order to collect data through a plurality of parallel slices. In another embodiment, the couch moves continuously such that the patient is scanned along helical paths. An x-ray tube 16 for emitting a fan shaped beam of radiation toward and spanning the scan circle 14 is mounted to a rotatable gantry 18. A collimator 20 mounted adjacent the x-ray tube is selectively adjustable to define the thickness of the fan shaped beam of radiation.

Figure 2:
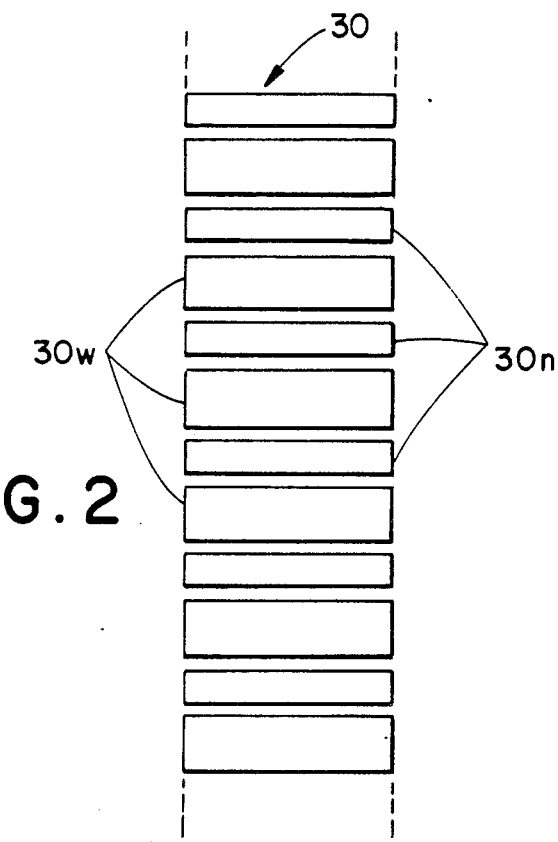
FIG. 2 is a detailed view from a center of the scan circle looking out at a segment of the detector ring.

With continuing reference to FIG. 1 and further reference to FIG. 2, a plurality of detectors 30 receive radiation that has traversed the scan circle 14. The detectors include a plurality of sets of detectors, each set of a preselected width in a peripheral direction around the scan circle. In the illustrated embodiment, there are alternate wide detectors $30_w$ and narrow detectors $30_n$. Optionally, detectors of one or more additional widths may also be placed in the detector array in a regular pattern.

Figure 3:
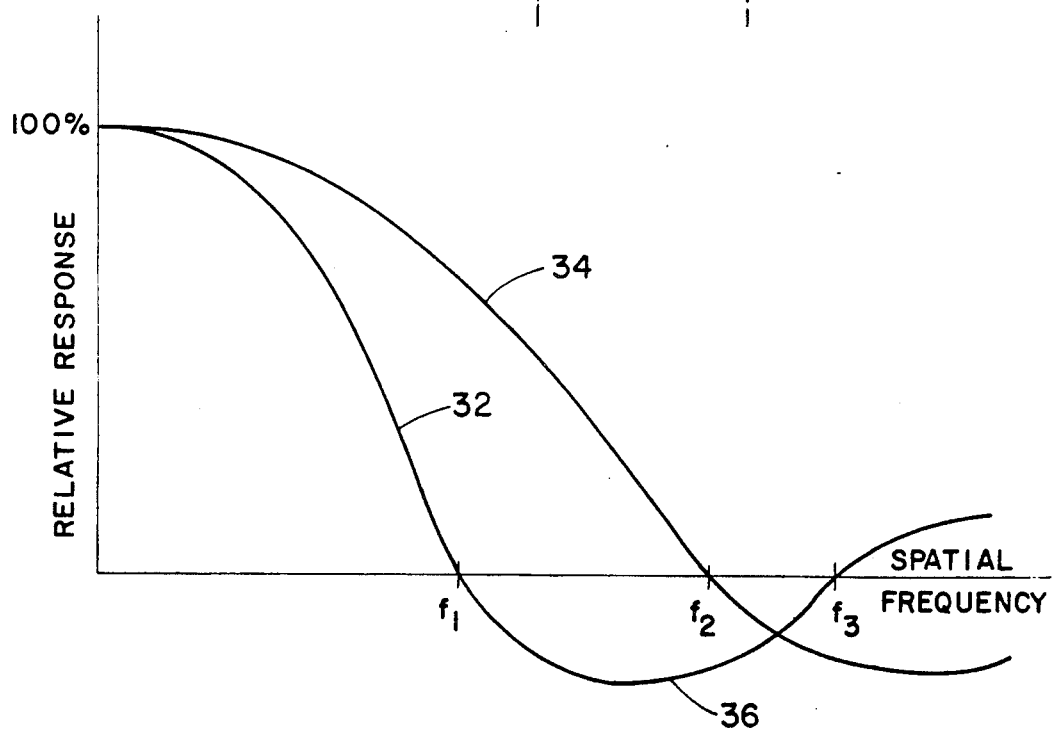
FIG. 3 is a diagrammatic illustration of the modulation transfer functions (MTF) expressed as a curve of relative response vs. spatial frequency for a wide detector, and a narrow detector.

With reference to FIG. 3, curve 32 illustrates the MTF of a wide detector, and curve 34 illustrates the MTF of a narrow detector. In this illustration it is assumed that the profile of the intensity of the x-ray beam is approximately rectangular, and thus the MTF curves have the approximate mathematical form of a sinc function (i.e. sin x/x). It should be noted that as the spatial frequency increases, the response of the wide detector falls off more rapidly than does the response of the narrow detector. Also there are certain crossover frequencies, for example f1 and f3 for the wide detector and f2 for the narrow detector, where the detector responses are zero. Furthermore, there are frequency regions where the detector response is finite but negative, that is where the phase is reversed. This phase reversal phenomena occurs between f1 and f3 for the wide detector, and between f2 and some higher frequency not shown on the plot for the narrow detector. It should be appreciated that if the frequency axis where extended to high frequencies in this plot, there would be many crossover points of zero response and regions of phase reversal because the curves oscillate about the frequency axis.

In a system where the detectors are of uniform width, the useful response of the system is limited to frequencies below the first zero crossover, i.e. below f1. One of the benefits of the multiple detector width configuration is that the response of a detector that extends beyond the first crossover frequency f1 and the phase reversal region can be utilized to improve overall detection performance. This benefit will become clear in the detailed description that follows.

With reference again to FIG. 1, a filter means 40 filters the analog output of the detector means 30. The analog outputs of the wide detectors $30w$ are filtered by filters $40w$, and the output of the narrow detectors $30n$ are filtered by filters $40n$. A sampling means 42 includes a wide detector sampling means $42w$ and a narrow detector sampling means $42n$ for sampling the output of the filter means $40w$ and $40n$, respectively. Filters $40n$ and $40w$ are typically low pass filters that reduce high frequency noise and signals that may cause aliasing as a result of discrete sampling. An analog-to-digital converter means 44 digitizes the sampled outputs of the wide and narrow detectors.

Figure 4:
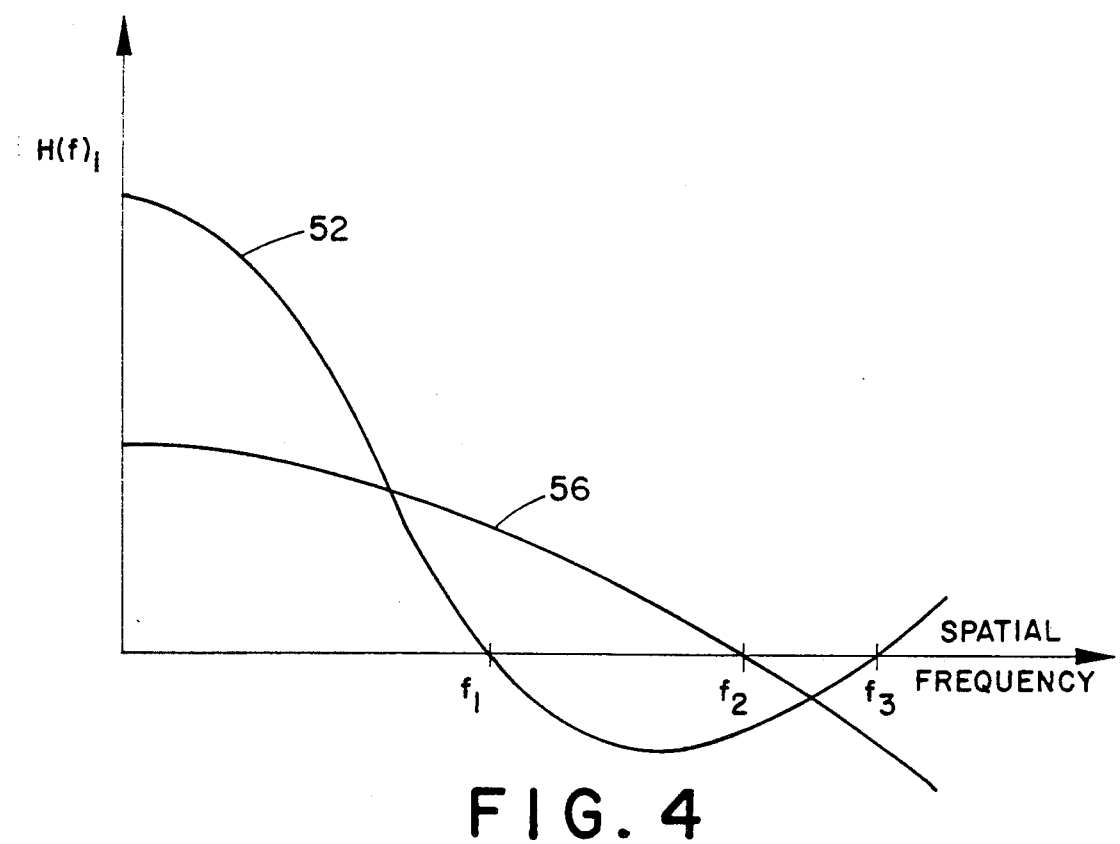
FIG. 4 illustrates exemplary filter functions for the narrow and wide detectors; and, FIG. 5 illustrates the signal to noise ratio (SNR) functions for a combination of a narrow and wide detector configuration, and a uniform detector configuration where the detector width is the average of the narrow and wide detector widths.

A digital filter means 50 operates on the digitized detector output signals. The digital filter means includes a wide detector means $50w$ and a narrow detector filter means $50n$. The capability of being able to filter the wide and narrow detector output signals with different filter functions is of significant benefit in optimizing the system response. For instance, the phase reversed response of the wide detector that occurs between frequencies f1 and f3 (curve segment 36 of FIG. 3) can be utilized to enhance the high frequency response of the system. By appropriate selection of the individual filter functions, the overall system signal to noise ratio can be optimized. FIG. 4 is a plot of a pair of typical filter functions. Curve 52 illustrates filter function $50w$ and curve 56 illustrates filter function $50n$. Notice that curve 52 has a negative range which inverts the phase reversed response of the wide detector, thus making it additive with the narrow detector response. Of course, other filter functions may be utilized, as are known in the art, to derive optimal filter functions for a given application for each signal and to optimize a composite response from both the wide and narrow detectors. A merging means 60 merges the individual sets of wide and narrow filtered detector signals into a composite set.

A second digital filter means 68 operates on the composite response with digital filters, as is known in the art, to adjust the composite modulation transfer function of the composite response signals to emphasize or deemphasize various frequency components, to adjust the noise spectrum and texture, and achieve other effects as are known in the art.

Figure 5:
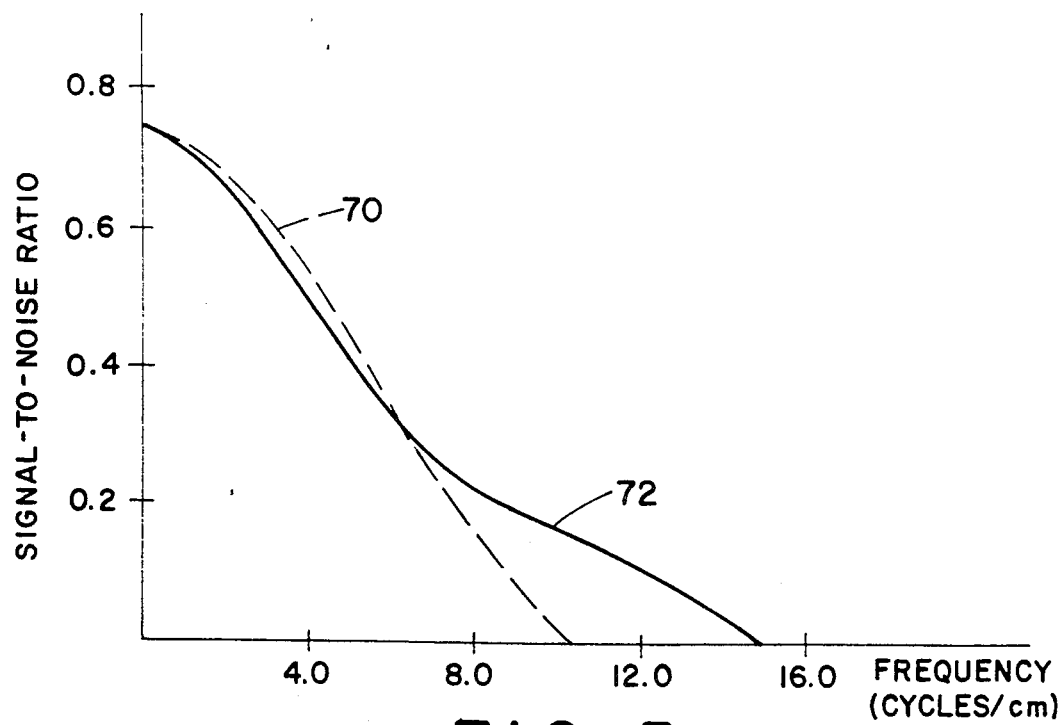

For purposes of comparison, the composite signal to noise ratio function of uniform width detectors whose widths are the average of the wide and narrow widths is illustrated in FIG. 5 as curve 70. Note that a composite signal to noise ratio function 72 of the preferred embodiment includes a significant higher frequency portion than the nominal width detector function 70.

This creates greater resolution in the resultant image than would be achieved with detectors of uniform average width.

A reconstruction means 80 reconstructs the digitized detector signals into an image representation. For example, the reconstruction means may include a convolution means 82 for convolving each digital signal with a filter function and a backprojecting means 84 for backprojecting the convolved or filter data lines into an image memory 86. Image representations stored in the image memory 86 are displayed on a video display terminal 88 or other display means, recorded on tape or disk for later retrieval, subject to image enhancement or other processing, and the like. The convolution function may be combined with the wide and narrow functions 50 and the digital filter 68 prior to the merging means 60 such that all are performed concurrently.

Looking to the mathematical support and theory behind this improvement, in prior art fourth generation CT scanners in which all detector apertures are of the same (uniform) width, the modulation transfer function (MTF) is approximately given by:

$$MTF_u = H(f)_u * sinc(SampD) * sinc(FSW) * sinc(DetW_u)$$

where:
u is the subscript denoting uniform detector width;
sinc(x) is short form of $$sinc(\pi f x) = \frac{sin(\pi f x)}{\pi f x}$$

SampD is the sampling distance and is given by $$\frac{FOVdia}{Nsamp}$$

FOVdia is the diameter of the "field of view"
Nsamp is the number of samples per detector.
FSW is the x-ray tube focal spot width referred to the center of the FOV and is given by the actual focal spot width multiplied by $$\frac{D}{S+D}.$$

D is the distance from the center of the FOV to the detectors (radius of detector ring).
S is the distance from the center of the FOV to the x-ray tube focal spot.
DetW$_u$ is the width of the detector aperture referred to the center and is given by the actual detector width (DETWID$_u$) multiplied by $$\frac{S}{S+D}.$$

H(f)$_u$ is the frequency filter function used to match spatial frequency and noise spectrum to the requirements of the particular application. In general, the filtering effects inherent in the reconstruction process (e.g., backprojector interpolation can be compensated for by H(f)$_u$. H(f)$_u$ is normalized to unity at f=0 [i.e, H(0)$_u$=1].

The noise power spectrum density (NPSD) of the projection data is $$NPSD_u \sim \frac{1}{NEQ_u} * H(f)_u^2 * Sp(f)$$

where:
NEQ$_u$ is the number of noise equivalent quanta of the detected radiation.
Sp(f) is noise spectrum. For the case of white noise, Sp(f) is flat [i.e., Sp(f)=1]
In a fourth generation CT scanner:

$$NEQ_u \sim M_u * DetW_u$$

where:
M$_u$ is the total number of detectors $$NPSD_u \sim \frac{H(f)_u^2}{NEQ_u} \sim \frac{H(f)_u^2}{M_u * DetW_u}$$

In evaluating the performance of CT imaging systems, it is meaningful to define a signal to noise ratio which relates MTF and NPSD as follows:

$$\frac{S}{N} = \frac{MTF}{\sqrt{NPSD}}$$

In the case of uniform detector width $$\left(\frac{S}{N}\right)_u \sim \frac{H(f)_u * sinc(SampD) * sinc(FSW) * sinc(DetW_u)}{\sqrt{\frac{1}{M_u * DetW_u} * H(f)_u^2}}$$

Disregarding constants of proportionality, $$\left(\frac{S}{N}\right)_u = sinc(SampD) * sinc(FSW) * sinc(DetW_u) * \sqrt{M_u * DetW_u}$$

Now consider the case of multiple detector widths, which will be denoted by the subscript MW. The MTF of a single detector channel of width, DetW$_i$, is given by $$MTF_i = H(f)_g sinc(SampD) * sinc(FSW) * sinc(DetW_i) * H(f)_i$$

The overall MTF is determined by summing the MTF's of each detector and normalizing to unity at f=0. Thus, $$MTF_{MW} = \frac{\sum_{i=1}^{I} M_i * MTF_i}{\sum_{i=1}^{I} M_i} = \frac{\sum_{i=1}^{I} M_i * MTF_i}{M_{MW}}$$

$$MTF_{MW} = \frac{H(f)_g * sinc(SampD) * sinc(FSW) * \sum_{i=1}^{I} [sinc(DetW_i) * H(f)_i]}{M_{MW}}$$

where
the subscript i denotes detectors of a particular width and I is the total number of different widths.
The subscript MW refers to the multiple detector width configuration.

$DetW_i$ is the width of the i detectors referred to the center of the FOV.

$M_i$ is the total number of i detectors $H(f)_i$ is the filter function used to filter the projection data of the i detectors.

$H(f)_g$ is a global filter function that is applied to all sets of projection data. The value of $H(f)_g$ is unity at $f=0$. $M_{mw}$ is the total number of detectors (i.e., $$M_{MW} = \sum_{i=1}^{I} M_i$$

Unlike the global filter function, the value of each $H(f)_i$ is not required to be unity at $f=0$; However, for proper normalization of $MTF_{MW}$:

$$\frac{\sum_{i=1}^{I} [M_i * H(o)_i]}{M_{MW}} = 1$$

The noise power spectrum of the projection data of an individual detector channel of detector width, $DetW_i$ is proportional to $$NPSD_i \sim \frac{H(f)_g^2 * H(f)_i^2}{NEQ_i} \sim \frac{H(f)_g^2 * H(f)_i^2}{DetW_i}$$

The overall NPSD is obtained by summing the individual $NPSD_i$ of each detector and normalizing by dividing by the square of the total number of detectors. Thus $$NPSD_{MW} = \frac{\sum_{i=1}^{I} M_i * NPSD_i}{M_{MW}^2} \sim \frac{H(f)_g^2}{M_{MW}^2} * \sum_{i=1}^{I} \frac{M_i * H(f)_i^2}{DetW_i}$$

the signal to noise ratio for the multiple detector width case is $$\left(\frac{S}{N}\right)_{MW} = \frac{MTF_{MW}}{\sqrt{NPSD_{MW}}}$$

Again, disregarding the constants of proportionality $$\left(\frac{S}{N}\right)_{MW} = \frac{sinc(SampD)*sinc(FSW)* \sum_{i=1}^{I} [M_i*H(f)_i*sinc(DetW_i)]}{\sqrt{\sum_{i=1}^{I} [M_i*H(f)_i^2/DetW_i]}}$$

Based on matched filter theory, the individual filter function $H(f)_i$, that optimizes the above signal to noise ratio is given by $$H(f)_x = \frac{M_{MW}*DetW_x*sinc(DetW_x)}{\sum_{i=1}^{I} M_i*DetW_i}$$

where the subscript x denotes a particular value of i. Note that the dc condition (i.e. freq=0) is met, that is $$\frac{\sum_{i=1}^{I}[M_i*H(o)_i]}{M_{MW}} = 1$$

and that the optimum signal to noise ratio $$\left(\frac{S}{N}\right)_{MW}(opt) = \frac{sinc(SampD)*sinc(FSW)* \sum_{i=1}^{I} M_i*DetW_i*sinc(DetW_i)^2}{\sqrt{\sum_{i=1}^{I} M_i*DetW_i*sinc(DetW_i)^2}}$$

$$\left(\frac{S}{N}\right)_{MW}(opt) = sinc(SampD)*sinc(FSW)*\sqrt{\sum_{(i=1)}^{I} M_i*DetW_i*sinc(DetW_i)^2}$$

With $\left(\frac{S}{N}\right)_{MW}$ optimized, $$MTF_{MW} = H(f)_g*sinc(SampD)*sinc(FSW) \frac{\sum_{i=1}^{I} M_i*DetW_i*sinc(DetW_i)^2}{\sum_{i=1}^{I} M_i*DetW_i}$$

and $$NPSD_{MW} = H(f)_g^2 \frac{\sum_{i=1}^{I} M_i*DetW_i*sinc(DetW_i)^2}{\left(\sum_{i=1}^{I} M_i*DetW_i\right)^2}$$

From the foregoing, it can be seen that a great deal of flexibility is provided in both design (e.g. in selecting the number and width of the detectors) and in customizing the scanning and reconstruction protocols for particular applications (e.g. selecting sampling and the individual filters, $H(f)_i$. To better understand and appreciate the significance of this flexibility, consider the following.

The global filter function $H(f)_g$, can be defined in such a manner to make the $MTF_{MW}$ or $NPSD_{MW}$ equivalent to that of a system with uniform detector widths.

To generate an $MTF_{MW}$ that is equal to that of a system comprised of uniform width detectors, $DetW_u$, the global filter function should be $$H(f)_{g(mtf)} = \frac{sinc(DetW_u)* \sum_{i=1}^{I} M_i*DetW_i}{\sum_{i=1}^{I} M_i*DetW_i*sinc(DetW_i)^2}$$

To generate a $NPSD_{MW}$ that has a flat frequency spectrum (i.e. white noise), requires $$H(f)_{g(n/s)} = \sqrt{\frac{\sum_{i=1}^{I} M_i * DetW_i}{\sum_{i=1}^{I} M_i * DetW_i * \text{sinc}(DetW_i)^2}} * H(f)_u$$

If, in addition, the equivalent $DetW_u$ is the average of all $DetW_i$, that is $$\sum_{i=1}^{I} M_i * DetW_i = M_u * DetW_u$$

then, the total number of detected quanta will be the same and thus both the magnitude and the spectrum of the NPSD will be identical between the multiple and uniform width detector configuration.

To illustrate the benefit of this invention, consider the case of the preferred embodiment of alternating two detector widths, $DetW_n$ and $DetW_w$ as illustrated in FIG. 2. In this case, $M_n = M_w = \frac{1}{2} M_{MW}$. The subscripts n and w indicate narrow and wide.

For optimum signal to noise, we have $$H(f)_n = \frac{M_{OR} * DetW_n * \text{sinc}(DetW_n)}{M_n * DetW_n + M_w * DetW_w}$$

$$H(f)_n = \frac{2 DetW_n * \text{sinc}(DetW_n)}{DetW_n + DetW_w}$$

similarly $$H(f)_w = \frac{2 DetW_w * \text{sinc}(DetW_w)}{DetW_n + DetW_w}$$

and $$\left(\frac{S}{N}\right)_{MW} (opt) = \text{sinc}(SampD) * \text{sinc}(FSW) *$$

$$\sqrt{\frac{M_{MW}}{2} DetW_n * \text{sinc}(DetW_n)^2 + DetW_w * \text{sinc}(DetW_w)^2]}$$

FIG. 5 illustrates a specific case where:
$M_u = 1200$
$M_n = 600$
$M_w = 600$ $$DetW_u = .23 \times \frac{64}{149} = .099 \text{ cm}$$

$$DetW_n = .15 \times \frac{64}{149} = .064 \text{ cm}$$

$$DetW_w = .31 \times \frac{64}{149} = .133 \text{ cm}$$

$$FSW = .06 \times \frac{85}{149} = .034 \text{ cm}$$

$$SampD = \frac{24}{1024} = .023 \text{ cm}$$

Note, at very low spatial frequencies, the signal to noise ratios are essentially equal. The multiple width signal to noise ratio is slightly lower than uniform detector width signal to noise ratio in the mid-frequency range (i.e. $1 < f < 7$), while the multiple width detector configuration has substantially higher signal to noise in the high frequency range, decreasing to zero at 15 lp/cm as compared to 10 lp/cm for the uniform case. Hence, for a small sacrifice in mid-frequency response, the multiple width configuration extends high frequency response by 50%.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the invention, the invention is now claimed to be:

1. A computerized tomographic scanner comprising:
   a source of penetrating radiation for projecting radiation through a scan circle;
   a ring or ring segment of radiation detectors at least partially circumscribing the scan circle, the ring of radiation detectors including detectors of at least two different radiation receptive widths in a direction around a periphery of the scan circle;
   a means for rotating the radiation source relative to the radiation detectors;
   sampling means for sampling output signals from the different width detectors;
   an image reconstruction means for reconstructing an image representation from the sampled output signals.

2. A computerized tomographic scanner comprising:
   a source of penetrating radiation for projecting radiation through a scan circle;
   a ring or ring segment of radiation detectors at least partially circumscribing the scan circle, the ring of radiation detectors including detectors of at least two different widths in a direction around a periphery of the scan circle;
   sampling means for sampling output signals from the different width detectors;
   a filtering means for filtering the sampled output signals from each width detector with a corresponding filter function;
   an image reconstruction means for reconstructing an image representation from the filtered output signals.

3. The scanner as set forth in claim 2 wherein the sampled output signal from a first of the detectors has a frequency response of a first phase at lower frequencies and a frequency response of an opposite phase at higher frequencies and wherein the filtering means includes means for reversing the phase of the opposite response.

4. The scanner as set forth in claim 3 further including a merging means for merging the sampled different width detector responses, the merging means being disposed between the filtering means and the image reconstruction means.

5. A CT scanner comprising:
   a source of penetrating radiation for providing a fan shaped swath of radiation through a scan circle for receiving a subject to be imaged;
   a means for rotating the fan shaped swath of radiation about the scan circle;
   a ring of radiation detectors surrounding the scan circle;
   a first sampling means for sampling outputs of a first plurality of the detectors;

a second sampling means for sampling outputs of a second plurality of the detectors;

a first filtering means for filtering the first detector outputs with a first filter function;

a second filtering means for filtering the second detector outputs with a second filter function, the second filter function being different from the first filter function;

a merging means for merging the filtered first and second sampled detector outputs to produce a composite signal;

an image reconstruction means for reconstructing the composite signal into an image representation.

6. The scanner as set forth in claim 5 wherein the sampled output signal from a first detector has a frequency response of a first phase at lower frequencies and a frequency response of an opposite phase at higher frequencies and wherein the first filtering means includes means for reversing the phase of the out of phase response.

7. The scanner as set forth in claim 5 wherein the detectors of the first and second pluralities of detectors are mounted alternately around the scan circle.

8. The scanner as set forth in claim 7 wherein the detectors of the first plurality of detectors have a different width from the detectors of the second plurality of detectors.

9. The scanner as set forth in claim 5 further including a digital filtering means for filtering the composite signal.

10. A method of generating diagnostic image representations, the method comprising:

rotating a beam of radiation around a scan circle in which a subject is disposed;

converting radiation which has traversed the scan circle and been received by a first plurality of detectors into a corresponding first set of signals;

converting radiation which as traversed the scan circle and been received by a second plurality of detectors into a corresponding second set of signals, the second plurality of detectors being different from and interleaved among the first plurality of detectors;

filtering the first set of signals with a first filter function;

filtering the second set of signals with a second filter function, the second filter function being different from the first filter function;

reconstructing the filtered sets of signals into the image representation.

11. A method of generating diagnostic image representations, the method comprising:

rotating a source of radiation around a scan circle in which a subject is disposed;

converting radiation that has traversed the scan circle along first paths from the radiation source to a first plurality of detectors of a first width into first radiation signals and converting radiation that has traversed the scan circles along second paths from the radiation source to a second plurality of detectors of a second width into a second plurality of signals, each of the first plurality of paths has a first resolution and each of the second plurality of paths has a second resolution, which second resolution is different from the first resolution;

filtering the first electrical signals with a first filter function and filtering the second signals with a second filter function;

reconstructing the filtered electrical signals into the image representation.

12. The method as set forth in claim 10 wherein in the filtering step, the electrical signals are filtered with digital filters.

13. A method of generating diagnostic image representations, the method comprising:

rotating a beam of radiation around a scan circle in which a subject is disposed;

converting radiation which has traversed the scan circle along different pluralities of paths into corresponding electrical signals;

filtering the electrical signal from each plurality of paths with a corresponding different filter function, one of the filter functions including a phase inverting portion for inverting a portion of the phase of a band of frequencies of one of the electrical signals, reconstructing the filtered electrical signals into the image representation.

14. The method as set forth in claim 12 further including merging the filtered electrical signals before reconstructing the image representation, such that the image representation is reconstructed from the merged filtered signals.

* * * * *